United States Patent [19]

Gunn

[11] Patent Number: 4,712,916
[45] Date of Patent: Dec. 15, 1987

[54] APPARATUS FOR INSPECTION OF THE WALLS OF DEEP HOLES OF MINUTE DIAMETER

[75] Inventor: John B. Gunn, Mt. Kisco, N.Y.
[73] Assignee: International Business Machines Corporation, Armonk, N.Y.
[21] Appl. No.: 695,509
[22] Filed: Jan. 28, 1985
[51] Int. Cl.[4] .................. G01N 21/88; G02B 23/24
[52] U.S. Cl. ........................... 356/241; 354/95
[58] Field of Search .................. 356/241; 350/96, 26; 128/4; 362/32; 354/62, 63, 95, 96

[56] References Cited

U.S. PATENT DOCUMENTS

| | | | |
|---|---|---|---|
| 3,551,061 | 12/1970 | Glowa | 356/241 |
| 3,610,763 | 10/1971 | Mathews | 356/241 |
| 3,733,138 | 5/1973 | Weinberg | 356/241 |
| 4,269,648 | 5/1981 | Dakss et al. | 156/293 |
| 4,288,159 | 9/1981 | Newman | 356/44 X |
| 4,422,719 | 12/1983 | Orcutt | 362/32 X |
| 4,566,789 | 1/1986 | Weber | 356/241 |

FOREIGN PATENT DOCUMENTS 2002136 2/1979 United Kingdom .

Primary Examiner—Vincent P. McGraw
Assistant Examiner—S. A. Turner
Attorney, Agent, or Firm—Roy R. Schlemmer

[57] ABSTRACT

The inspection of the walls of a deep hole of minute diameter in a structure such as an integrated circuit board is carried out by inserting into the hole a reflective optical sphere having a diameter at least slightly smaller than the hole diameter. A coated optical fiber having a diameter substantially less than the diameter of the sphere has one end attached to the sphere. An optical scattering means is interposed between the sphere and the fiber to disperse illumination from the optic fiber to illuminate the walls of the hole. A source of illumination is provided at the opposite end of the optic fiber, and an optical system is positioned axially at the end of the hole to pick up the image of the illuminated walls reflected from the sphere.

1 Claim, 3 Drawing Figures

APPARATUS FOR INSPECTION OF THE WALLS OF DEEP HOLES OF MINUTE DIAMETER

DESCRIPTION

Technical Field

There is an important need for the inspection of the interior surfaces of minute holes in structures such as printed circuit boards. Not only are these holes often very small in diameter, but the ratio of the length to the diameter (aspect ratio) is frequently 10 to 1, or more. For instance, the holes may be as small 0.4 millimeters, and the length of the hole as much as 4 millimeters, or more. This high aspect ratio makes it impossible to use any of the conventional bore inspection microscopes for inspection of the walls of these minute holes.

One of the most serious problems in this connection is to adequately illuminate the walls of the hole under inspection. That is particularly serious in the case of blind holes, those which do not go all the way through the circuit board.

Another important and serious problem is that the surfaces to be inspected are essentially perpendicular to the direction of view.

Summary of the Invention

Accordingly, it is one important object of the present invention to provide an improved apparatus for the inspection of high aspect ratio holes of minute diameter.

Another object of the invention is to provide an improved means for transmitting optical images of the wall surfaces of minute holes for inspection purposes.

Another object of the invention is to provide an improved means for illumination of localized portions of the walls of minute holes which are under inspection for the transmission of an image of those walls.

Further objects and advantages of the invention will be apparent from the following description and the accompanying drawings.

In carrying out the invention there is provided an apparatus for the inspection of the walls of a deep hole of minute diameter in a structure such as an integrated circuit board comprising a reflective optical sphere having a diameter at least slightly smaller than the hole diameter, a coated optical fiber having a diameter substantially less than the diameter of said sphere and having one end attached to said sphere for manipulation of said sphere in the hole, an optical scattering material interposed between said sphere and said fiber to disperse illumination from the optic fiber to illuminate the walls of the hole, a source of illumination at the opposite end of said optic fiber, and an optical system positioned axially at the end of said hole to pick up the image of the illuminated walls reflected from said sphere.

DETAILED DESCRIPTION OF PREFERRED EMBODIMENTS

Figure 1:
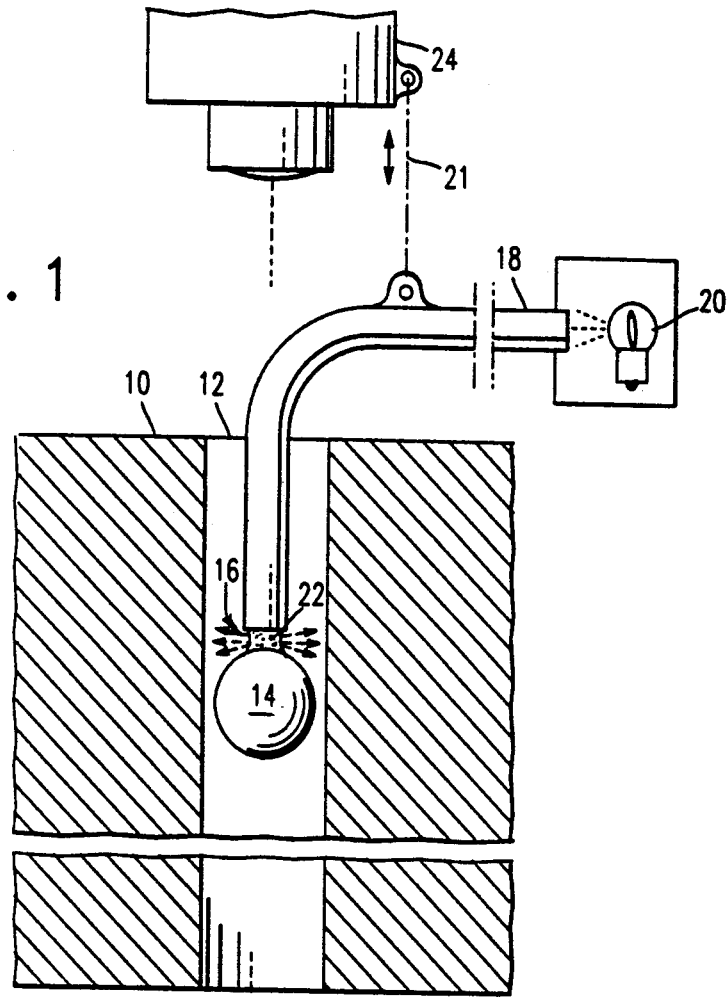
FIG. 1 is a schematic representation, partly in section, and greatly enlarged, illustrating a preferred form of the invention.

Referring more particularly to FIG. 1, there is illustrated a circuit board 10 including a hole 12 to be inspected. In order to illustrate the invention more clearly, the thickness of the circuit board 10 has been foreshortened so that the length of the bore of the hole is illustrated at only about half its possible total length in relation to its diameter. The apparatus in accordance with this invention for accomplishing the inspection of the hole 12 includes a reflective spherical ball 14 which is attached by means of an adhesive 16 to the end of a coated optical fiber 18. Illumination is supplied through the optical fiber 18 to the vicinity of the spherical ball 14 by means of a light source schematically illustrated at 20. The adhesive 16 is preferably a substantially clear or light transmissible adhesive, and has embedded therein microscopic light-scattering (sometimes referred to below as optical scattering) particles 22. The particles cause dispersion of the light traveling through the light pipe 18 to illuminate the walls of the hole 12 just above the sphere 14. The image of the illuminated section of wall is reflected from the upper surfaces of the sphere 14 to a microscope 24.

The reflective sphere 14 is preferably highly polished so as to provide good optical reflective properties. For this purpose, it has been found that a commercially available stainless steel roller bearing ball is very useful. A tungsten carbide ball has also been found to be very useful. Such balls are available in many sizes, including very minute sizes. The sphere 14 should preferably fit closely within the bore of the hole 12 so as to be positioned and centered within the bore by the walls of the hole. The optic fiber 18 preferably has a diameter which does not exceed more than about one third the diameter of the sphere 14.

The clear adhesive attaching the optic fiber to the sphere 14 is preferably composed of a clear epoxy plus a reactive setting agent for that epoxy. The light-scattering particles 22 included within the adhesive may be composed of various different materials. However, the preferred material is alumina in a particle size of about one micron. That material has been found to be very satisfactory. The microscope 24 may be of conventional construction.

In operation, the sphere 14 is moved axially in the bore of the hole 12 by manipulating the optic fiber 18. The microscope 24 is moved in synchronism with the movement of the sphere 14, as schematically indicated by the connection shown between the microscope 24 and the optic fiber 18 at 21. It will be understood that the circuit board may be moved vertically with relation to the sphere 14 and the microscope 24, rather than moving the sphere and the microscope.

Figure 2:
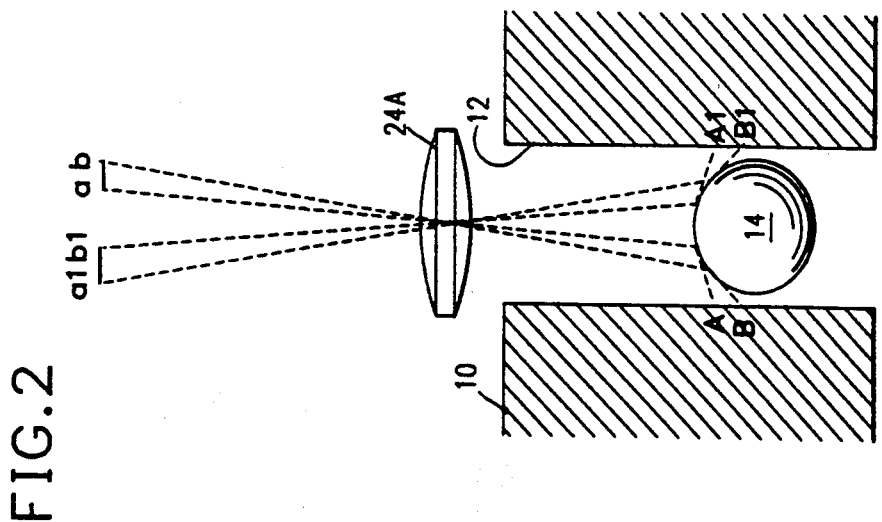
FIG. 2 is a schematic representation illustrating the operation of the optical system in the embodiment of FIG. 1.

FIG. 2 illustrates the optical principles involved in the combination of the spherical reflector 14 and the microscope 24. The cylindrical area of the wall of the hole 12 which is illuminated by the light pipe is indicated in FIG. 2 by the letters A-B on the left and by A1-B1 on the right. This illuminated cylindrical ring area is reflected by the upper surfaces of the sphere 14 and focuses through the microscope lens 24A to an image plane indicated at the top of the drawing in a ring identified on the left by the symbols b1-a1, and on the right by the symbols a-b.

Thus, the observer using the microscope 24 is presented with a ring image representative of the illuminated cylindrical section of the hole which is under inspection. By moving the sphere 14 up and down within the bore of the hole 12, the entire bore may be inspected. The image as viewed through the microscope is substantially enlarged, so that the observer is provided with an accurate indication of any defects in the walls of the hole.

Figure 3:
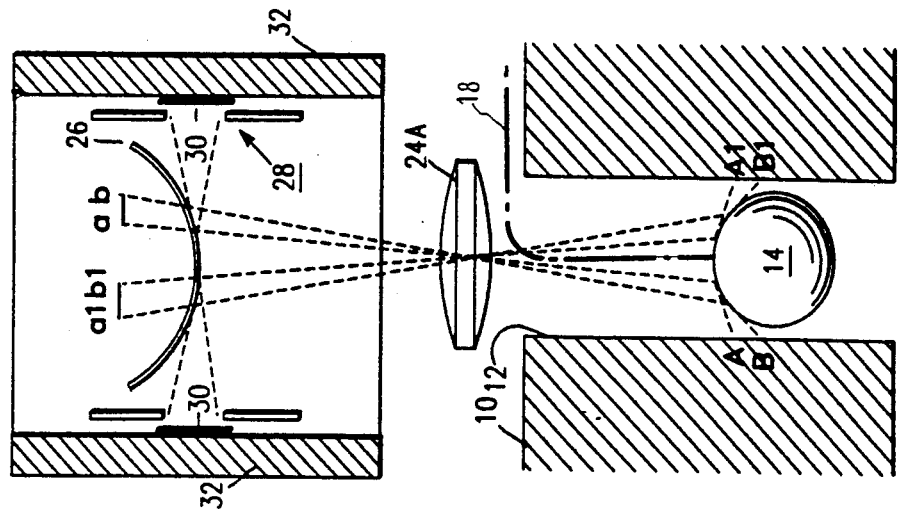
FIG. 3 is a representation corresponding to that of FIG. 2, but illustrating an alternative embodiment of the invention.

FIG. 3 illustrates a modification of the invention in which a second spherical reflector 26 is positioned beneath the plane of the image b1-a1 and a-b and arranged to reflect the image through an optical aperture slit 28 and onto a cylindrically arranged photographic film 30 which is supported by a film support 32. Again, in this embodiment, the entire microscope assembly, including the lens 24A and the spherical reflector 26 and the structure of the aperture 28 is vertically movable in synchronism with the sphere 14 in relation to the walls of the hole 12. The film support 32 is movable in a synchronized fashion in an opposite sense to accommodate for the movement of the image in the axial direction. By this vertical synchronous movement, the walls of the hole 12 are scanned and are synchronously recorded upon the cylinder 30 of photographic film. When the film is developed and rolled out, a developed view of the inside of the walls of the hole 12 is presented.

Referring back again to FIG. 1, it has been found that the presence of the optical fiber 18 in the path of the light reflected from the sphere 14 to the first lens of the microscope is not serious. While the optic fiber may have a diameter as large as one third the diameter of the sphere 14, that means the area of the optic fiber is only one ninth of the total area of the bore of hole 12. Furthermore, the ring shaped image which is under observation is observed through an optical path which largely avoids the central portion of the bore where the optical fiber is positioned.

It is very desirable that the adhesive 16 with the light-scattering particles 22 should not be present in large volume. For one thing, the adhesive mass should not overlap the outside edges of the optic fiber at the end of attachment to thereby avoid dispersion of the light onto upper wall areas for which the image is not as effectively reflected by the sphere 14. That disadvantage is avoided by restricting the mass of the adhesive so that the solidified adhesive does not have an axial length which substantially exceeds the diameter of the optic fiber. Accordingly, it is preferred to limit the volume of the adhesive to no more than a volume corresponding to a cylinder having the same diameter as the optic fiber and an axial length equal to the diameter. By so limiting the volume of the adhesive, the band of dispersion of light from the end of the optic fiber is appropriately limited to a particularly useful band area of the inner bore of the hole 12. While the spherical reflector 14 is theoretically capable of reflecting an image of substantially the entire wall surface of the hole 12 above the spherical reflector, there is a substantial distortion of the image in the regions more distant from the spherical reflector 14. Accordingly, it has been found to be most useful to illuminate and observe a more restricted portion of the wall surface at any one time.

The sphere 14 is preferably very close in outside diameter to the inside diameter of the hole 12 so that it is precisely positioned within that hole by the walls of the hole. Thus, for instance, the diameter of the sphere may be ideally equal to about 93% of the diameter of the hole.

One of the most important features of the invention is in the provision of the light-scattering particles 22 within the adhesive 16. Without those particles, most of the light transmitted through the light pipe 18 is directly reflected by the sphere back up the light pipe 18, without reaching the walls of the hole to be inspected. In a larger structure, other means might be used for dispersion of the light such as a conical reflector aligned with the axis of the light pipe 18. But such a structure is quite elaborate and expensive as compared with the light dispersion particles in the adhesive, and is virtually impossible to implement in a structure as small as that contemplated in the present invention.

The volume of the light-scattering particles 22 within the body of the cement 16 is not critical. However, it is believed that the volume of those particles should be at least in the order of five to ten percent.

In carrying out the invention, and in joining the end of the light pipe to the sphere with the epoxy glue, a clear epoxy glue having two constituents, is preferred, and one which does not set up rapidly. That is, one which sets up in hours rather than minutes.

In one embodiment of the invention, the material used for the optic fiber was obtained from Dupont under the trademark name Crofon. It was a clad plastic fiber having a diameter of 0.127 millimeters. An additional cladding was added to the fiber to reduce light leakage. The end of the fiber was then cut off as square as possible, the epoxy was mixed, and a drop of the epoxy was touched to the end of the fiber to leave an approximately hemispherical droplet at that end, care being taken to prevent the epoxy from getting onto the sides of the fiber. A few small clumps of the light-scattering alumina particles were then touched to the epoxy and eventually were drawn in by surface tension.

After all of the particles were wetted, the epoxyed end of the fiber was carefully touched to the surface of the sphere to establish the attachment. A micromanipulator device is useful for this operation. The fiber was then suspended vertically, with the sphere beneath the end of the fiber, so that gravity and the surface tension of the adhesive caused the axis of the sphere to align with the axis of the fiber.

While this invention has been shown and described in connection with particular preferred embodiments, various alterations and modifications will occur to those skilled in the art. Accordingly, the following claims are intended to define the valid scope of this invention over the prior art, and to cover all changes and modifications falling within the true spirit and valid scope of this invention.

Having thus described the invention, what is claimed as new, and desired to secure by Letters Patent is:

1. Apparatus for the inspection of the walls of a deep hole of minute diameter in a structure such as an integrated circuit board comprising a reflective optical sphere having a diameter at least slightly smaller than the hole diameter, a single coated optical fiber having a diameter substantially less than the diameter of said sphere and having one end attached to said sphere for manipulation of said sphere in the hole, an optical scattering means interposed between said sphere and said fiber to disperse illumination from the optic fiber to illuminate the walls of the hole, a source of illumination at the opposite end of said optic fiber, and an optical system positioned axially at the end of said hole to pick up the image of the illuminated walls reflected from said sphere, said optical system including at least one lens and a second spherical reflector arranged beyond said lens for reflecting images focused through said lens from said first-mentioned sphere radially outwardly, a cylindrical slip aperture positioned to transmit a selected axial length of the illuminated image of the cylindrical wall being inspected as reflected from said second spherical reflector, a photographic film arranged in a cylindrical configuration in axial alignment with the hole to be inspected, and means for synchronously moving said film along an extension of the axis of said hole in synchronism with movement of said image axially within said hole to thereby generate a photographic record of the appearance of the inside wall of the hole.

* * * * *